US010422739B1

(12) United States Patent
Van Derslice et al.

(10) Patent No.: US 10,422,739 B1
(45) Date of Patent: *Sep. 24, 2019

(54) REFLECTOMETER, SPECTROPHOTOMETER, ELLIPSOMETER AND POLARIMETER SYSTEMS WITH A SUPER CONTINUUM LASER SOURCE OF A BEAM OF ELECTROMAGNETISM, AND IMPROVED DETECTOR SYSTEM

(71) Applicant: J.A. WOOLLAM CO., INC, Lincoln, NE (US)

(72) Inventors: Jeremy A. Van Derslice, Lincoln, NE (US); Martin M. Liphardt, Lincoln, NE (US)

(73) Assignee: J.A. WOOLLAM CO., INC., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/350,017

(22) Filed: Sep. 12, 2018

Related U.S. Application Data

(63) Continuation-in-part of application No. 14/757,280, filed on Dec. 14, 2015, which is a continuation-in-part of application No. 15/330,430, filed on Sep. 20, 2016, now Pat. No. 10,132,684, which is a continuation-in-part of application No. 14/757,280, filed on Dec. 14, 2015.

(60) Provisional application No. 62/124,428, filed on Dec. 18, 2014, provisional application No. 62/284,441, filed on Sep. 30, 2015.

(51) Int. Cl.
*G01N 21/21* (2006.01)
*G01J 3/447* (2006.01)

(52) U.S. Cl.
CPC ............ *G01N 21/211* (2013.01); *G01J 3/447* (2013.01); *G01N 2021/213* (2013.01)

(58) Field of Classification Search
CPC .................................................... G01N 21/211
USPC ........................................................ 356/326
See application file for complete search history.

(56) References Cited

U.S. PATENT DOCUMENTS

| 5,963,327 A | 10/1999 | He | G01J 3/447 |
| | | | 250/225 |
| 6,104,488 A | 8/2000 | LeVan | |
| | | (Continued) | |

OTHER PUBLICATIONS

A New Spectrumeter Using Multiple Gratings With a Tw-Dimensional Charge Coupled Diode Array Detor, Han et al., Rev. Sci.Inst. vol. 74 No. 6, (Jun. 2003).

(Continued)

*Primary Examiner* — Tarifur R Chowdhury
*Assistant Examiner* — Omar H Nixon
(74) *Attorney, Agent, or Firm* — James D. Welch

(57) ABSTRACT

Reflectometer, spectrophotometer, ellipsometer, and polarimeter systems having a supercontinuum laser source of coherent electromagnetic radiation over a range of about 400-about 2500 nm, a stage for supporting a sample and a detector of electromagnetic radiation, wherein the supercontinuum source provides a coherent beam of electromagnetic radiation which interacts with a sample, and the detector system comprises functional combinations of gratings and/or combination dichroic beam splitter-prisms, which themselves can be optimized as regards wavelength dispersion characteristics, directs wavelengths in various ranges to various detectors that are well suited to detect them.

36 Claims, 9 Drawing Sheets

(56) References Cited

U.S. PATENT DOCUMENTS

| | | | |
|---|---|---|---|
| 6,895,149 B1 | 5/2005 | Jacob et al. | |
| 7,345,762 B1 | 3/2008 | Liphardt et al. | |
| 7,522,331 B2 | 4/2009 | Lapchuk et al. | |
| 7,570,358 B2 | 8/2009 | Den Boef | |
| 8,031,337 B2 | 10/2011 | Den Boef | |
| 8,169,611 B2 | 5/2012 | Herzinger et al. | |
| 8,422,519 B2 | 4/2013 | Knight et al. | |
| 8,441,639 B2 | 5/2013 | Kandel et al. | |
| 8,643,841 B1 * | 2/2014 | Rotter | G01J 3/36 356/326 |
| 8,718,104 B2 | 5/2014 | Clowes et al. | |
| 8,873,054 B2 | 10/2014 | Kandel et al. | |
| 9,080,971 B2 | 7/2015 | Kandel et al. | |
| 2006/0238743 A1 | 10/2006 | Lizotte et al. | |
| 2008/0117413 A1 | 5/2008 | Liphardt | G01N 21/211 356/73 |
| 2008/0239265 A1 | 10/2008 | Den Boef | |
| 2008/0279442 A1 | 11/2008 | Den Boef | G03F 1/84 382/144 |
| 2009/0262366 A1 | 10/2009 | Den Boef | |
| 2011/0031414 A1 * | 2/2011 | Lippert | G02B 21/002 250/459.1 |
| 2011/0069312 A1 | 3/2011 | Kandel et al. | |
| 2011/0109906 A1 | 5/2011 | Liphardt | G01N 21/01 356/400 |
| 2012/0057158 A1 | 3/2012 | Hilfiker | G01N 21/211 356/369 |
| 2012/0071342 A1 * | 3/2012 | Lochhead | G01N 21/6452 506/9 |
| 2013/0010365 A1 | 1/2013 | Curtis | |
| 2013/0027673 A1 | 1/2013 | Moussa | |
| 2013/0182263 A1 | 7/2013 | Shchegrov | G01B 9/02 356/512 |
| 2013/0203627 A1 * | 8/2013 | Moll | G01N 21/6486 506/9 |
| 2013/0222795 A1 | 8/2013 | Madsen | G01B 11/0625 356/237.5 |
| 2013/0304408 A1 * | 11/2013 | Pandev | H01L 22/20 708/83 |
| 2014/0233091 A1 | 8/2014 | Clowes et al. | |
| 2015/0036142 A1 | 2/2015 | Kandel et al. | |
| 2015/0046118 A1 | 2/2015 | Pandev | |
| 2015/0046121 A1 | 2/2015 | Dziura | |
| 2015/0058813 A1 | 2/2015 | Kim | |
| 2015/0323316 A1 | 11/2015 | Shchegrov et al. | |
| 2015/0330770 A1 | 11/2015 | Poslavsky | |

OTHER PUBLICATIONS

Optotune Data Sheet—Electroactive Polymer and Reluctance Force LSR.

* cited by examiner

Speckle reduction measured with a CCD camera

Speckle reduction measured with a CCD camera

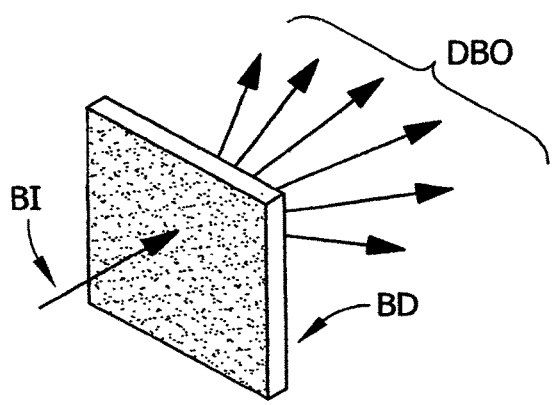
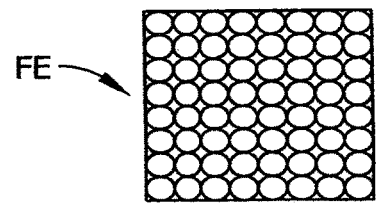
Fig. 10a     Fig. 10b
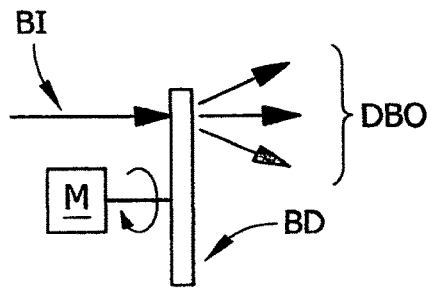
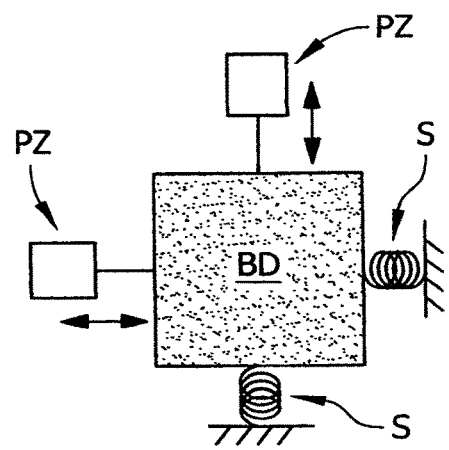
Fig. 10c     Fig. 10d

REFLECTOMETER, SPECTROPHOTOMETER, ELLIPSOMETER AND POLARIMETER SYSTEMS WITH A SUPER CONTINUUM LASER SOURCE OF A BEAM OF ELECTROMAGNETISM, AND IMPROVED DETECTOR SYSTEM This Application is a CIP of application Ser. No. 15/330,430 Filed Sep. 20, 2016 and therevia Claims benefit of Provisional 62/844,441 Filed Sep. 30, 2016, and is also a CIP of Ser. No. 14/757,280 Filed Dec. 14, 2015, and therevia Claims Benefit of Provisional Application Ser. No. 62/124,428, filed Dec. 18, 2014, and further directly Claims Benefit of Application Ser. No. 62/284,441 filed Sep. 30, 2015.

TECHNICAL FIELD

The present invention relates to sample investigation systems that utilize electromagnetic radiation, and more particularly to reflectometer, spectrophotometer, ellipsometer, and polarimeter systems comprising a supercontinuum laser source of electromagnetic radiation, a stage for supporting a sample and a detector of electromagnetic radiation over a range of about 400-2500 nm. The present invention is distinguished in that it applies a beam of high intensity, highly directional electromagnetic radiation provided by said super continuum laser, and applies detector systems that direct wavelengths, via functional combinations of gratings and/or combination dichroic beam splitter-prisms, (which can be optimized as regards wavelength dispersion characteristics), in various ranges with various detectors that can be optimized to detect them.

BACKGROUND

The use of electromagnetic radiation to investigate samples is well known. Reflectometer, spectrophotometer, ellipsometer, and polarimeter systems, for instance, direct a beam of electromagnetic radiation to interact therewith, (in reflection and/or transmission), a sample, which beam then enters a detector. Detected changes in Intensity (in reflectometer and spectrophotometer systems), and Polarization State (in ellipsometer, and polarimeter systems), as a result of said interaction provide insight to properties of the sample. Properties such as absorption constant, ellipsometric Psi and Delta etc. are evaluated, typically by performing a mathematical regression of accumulated data onto a mathematical model of the sample.

It is always of benefit to investigate a sample with multiple angles-of-incidence of the beam to a sample surface, and with as many wavelengths as possible. In the later is found a major innovation of the present invention which identifies and applies as a source of a beam of electromagnetic radiation a supercontinuum laser. Briefly, as described in an Article titled "Supercontinuum", said terminology "supercontinuum laser" refers to a source of electromagnetic radiation that results from interaction of a typically pulsed laser and many non-linear processes to cause extensive spectral broadening. (Note, "extensive" means beyond a single wavelength, and in the present invention it can be interpreted to mean a spectrum between about 400 to about 2500 nm. Non-linear processes include self-phase modulation, four-wave mixing, soliton dynamics and cross-phase modulation. (The term "soliton" refers to relatively permanent localized waveforms that are formed from dispersion and non-linearity effects. For instance, the refractive index of a material at a given frequency depends on the amplitude of electromagnetic radiation applied, (ie. the non-linear Kerr effect). If a pulse has the right shape said Kerr effect will exactly cancel dispersion in the material and the pulse's shape will not change over time, thereby forming a "soliton". Also, the term "four-wave mixing" refers to the effect wherein interaction between two or three wavelengths produces additional new wavelengths, (eg. a non-linear interaction of two different wavelength beams affect a third wavelength beam such that a fourth wavelength beam is generated). Continuing, said "Supercontinuum" article provides that the two most important regimes are soliton fusion and modulation instability, and that a third regime involves pumping in the normal, (ie. refractive index decreases with increase in wavelength), dispersion region. Soliton fusion involves application of a high powered femto-second pulse being launched into highly non-linear photonic crystal, or other highly non-linear fiber, where the femto-second pulse can be considered a high order soliton which rapidly broadens and then fissions into fundamental solitons. The resulting fundamental solitons then undergo intra-Raman scattering and shift to longer wavelengths, (known as soliton a self-frequency shift), which generates a long wavelength side of a continuum. A sorter wavelength side of a continuum is formed when longer soliton self frequencies as dictated by group velocity matching conditions via a soliton trapping mechanism. This approach to producing a supercontinuum is characterized by the production of high temporal coherence. A disadvantage of this approach is that high average powers in the produced continuum are not achievable. The modulation instability regime involves the breakup of a continuous or quasi-continuous wave field. The long-wavelength side of the continuum formed in this regime is generated by intra-pulse Raman scattering and self frequency sifting. The short wavelength side is generally attributed to soliton fission and dispersive wave generation. The normal dispersion range pumping approach, where pulses are short enough, is attributed to self-modulation which can lead to significant broadening which is temporarily coherent. Where pulses are not ultra-short then stimulated Raman scattering tends to dominate and typically a series of cascaded discrete Stokes lines will appear until the zero dispersion wavelength is reached. At this point a soliton Raman continuum can form. Pumping in the anamolous range is more efficient for continuum generation. For insight it is noted that the normal pumping range dispersion is that in which an increase in wavelength leads to a decrease in refractive index. This relationship is the opposite in the anamolous range. For an increase in wavelength the refractive index increases. For additional insight, Raman scattering of photons is inelastic, and mediated by an exciton. Only 1 in about 10 million photons that are scattered from a molecule or atom are scattered by the inelastic Raman effect, but those that are present at a different frequency than was the initial photon, and the wavelength of the scattered photon is usually longer, therefore the scattering molecule, for instance, can be excited to a higher energy level by the interaction.

While the formation of a supercontinuum laser spectrum is the result of many complex non-linear effects, such need not concern us as regards the present invention which is not dependent on how a supercontinuum is produced, only that it is and is applied in such as a reflectometer, spectrophotometer, ellipsometer or polarimeter.

An additional effect that must also be considered is the result of coherence that results in a supercontinuum range of wavelengths. When coherence is present it is very well known that interference effects result based on differences in phase between interacting waves. When lasers are involved the effects of interference is often referred to as "Speckle" and importantly this leads to time varying beam profiles. To be conveniently applied in a system such as a reflectometer, spectrophotometer, ellipsometer or polarimeter the complexity entered by such spatial and temporal fluctuations must be reduced. The present invention therefore applies speckle reducers, such as Optotune Elastoactive Polymer and Reflective Force LSR's.

Turning now to Identified Patent literature that has relevance regarding Supercontiuum Laser Sources, the following were identified:

U.S. Pat. No. 8,422,519 to Knight et al.;
U.S. Pat. No. 8,718,104 to Clowes et al.; and
Published App. No. 2014/0233091 by Clowes et al.

The present invention also involves application of improved detector systems. In that light, it is emphasized that it is well known to apply detectors of electromagnetic radiation in, for instance, ellipsometry. And it is known to use beam splitters to direct portions of beams into different detectors which can be optimized to respond to different wavelength ranges. A Patent to Herzinger et al. U.S. Pat. No. 8,169,611, for instance shows such an arrangement in FIG. 1a thereof. Many other references showing similar application of beam splitters in a similar manner exist. Also known are monochromater systems that utilizes a sequence of gratings with which a beam of spectroscopic electromagnetic radiation sequentially interacts to select a desired wavelength. FIG. 9 in a Patent to Liphardt et al. U.S. Pat. No. 7,345,762 provides an example that shows such an arrangement, and FIG. 2 in said Patent 762 also demonstrates an ellipsometer or polarimeter system.

Another known Patent is U.S. Pat. No. 6,104,488 to LeVan. This Patent is focused on providing high single grating efficiency, with different orders of wavelengths being produced thereby detected by a single detector.

An article titled "A New Spectrometer Using Multiple Gratings With A Two-Dimensional Charge-Coupled Diode Array Detector", Review of Scientific Instruments, Han et al., Vol. 74, No. 6, June 2003, describes a special grating that consists of three laterally stacked sub-gratings to generate three wavelength ranges.

Additional Patent references identified in a computer Search are:

Searching for (Supercontinuum Laser and Ellipsometer) provided five Patents, U.S. Pat. Nos. 9,080,971, 8,873,054, 8,441,639, 8,031,337 and 7,570,358, and six Published Applications, No. 2015/0323316, 2015/0036142, 2013/0222795, 2011/0069312, 2009/0262366 and 2008/0239265; and Searching of (Supercontinuum & Laser and Ellipsometer and Speckle) provided no Patents and only four Published Applications, Nos. 2015/0058813, 2015/0046121, 2015/0046118 and 2015/0330770.

Also, known Patents and Published Applications relating to Spekle Reduction are: U.S. Pat. No. 6,895,149 to Jacob et al.; U.S. Pat. No. 7,522,331 to Lapchuk et al.; US 2013/0027673 by Moussa; US 2006/0238743 by Lizotte et al. and US 2013/0010365 by Curtis.

Further, in prosecution of Parent application Ser. No. 14/757,280 the Examiner identified:

Hilfiker et al. US2012/0057158;
Herzinger US2013/0026368;
Pandev US2013/0304408;
Ostermeyer US2013/0268336;
Johs US2015/0219497;
Moriva et al. US2009/0267003;
Grejeda US2014/0304963;
Yamaguchi et al. US2013/0063700.

In particular the Pandev 408 reference is relevant in that it mentions, in passing, use of a Super Continuum Laser Source as an example of a source of electromagnetic radiation. However, that use is in a pathway that directs a beam produced thereby to interact with both a Beam Splitter and an Objective Lens prior to interacting with a Sample. While Pandev 408 suggests possible application of a Super Continuum Laser Source as just described, it does not suggest application in a pathway which approaches a Sample at an Oblique Angle-of-Incidence and which does not pass through a Beam Splitter and an Objective Lens along the way. This is important as had Pandev 408 intended such an application it seems it would have mentioned it. This is because Pandev 408 includes a Beam from a separate Source, labeled, (102) in Pandev 408), which does involve a Beam approaching a Sample (201) at an Oblique Angle-of-Incidence. No suggestion that the Illuminator (102) should be a Super Continuum Laser (202) is present in Pandev 408, however. Had it been intended that Illuminator (102) be a Super Continuum Laser (202), Pandev 408 should have mentioned it! It is emphasized at this point, that the Present Invention involves a an Electromagnetic Beam approaching a Sample at an Oblique Angle-of-Incidence, which Beam does not pass through combination of a Beam Splitter and an Objective Lens, in that order. This cannot be over-emphasized!

It is noted as well that the Herzinger 368 and Hilfiker et al. 158 references were cited in the prosecution of Parent application Ser. No. 14/756,345 as serving to show sources of electromagnetic radiation which provide wavelengths in a range overlapping that of a Super Continuum Laser, are sufficient as references against said 345 Parent Application as regards System Claims. The 345 Application however, did not provide support for a negative limitation regarding a combination Beam Splitter and Objective Lens, (elements (205) and (206) in Pandev 408, respectively, in Claims, hence necessitating the present CIP which provides the required support. Further, it is noted that Herzinger 368 specifically listed Sources for use in the invention, and gave no incentive to one skilled in the art to seek out other Sources. Hilfiker et al. 158 did not so list Sources, and shows a range of 200-1000 nm as exemplarly in its FIGS. 6c-6e. This range overlaps that of about 400 to about 2500 nm as recited in the present Application, and in the Parent application Ser. No. 15/330,430. The Examiner, in the 430 Application Prosecution cited Hilfiker et al. 158 as valid art against, because of the wavelength range overlap in view of In re Wertheim 541 F.2d 257m 191 USPQ 90 (CCPA 1976) 2144.05(i). As a precaution, it is stated that the Present Claims can be amended to cover only a limited range of wavelengths of between—more than 1000 to about 2500 nm, if necessary. However, in view of the negative limitation in the Present Claim 1, regarding a combination Beam Splitter and Objective Lens, (elements (205) and (206) in Pandev 408, this is believed unnecessary. Applicant reserves the right to recite any other reduced wavelength range should that be necessary to avoid a presently un-cited reference. It is believed Pandev 408 is removed as a reference thereby, and that is the only reference cited that even suggests use of a super continuum laser that, it is disclosed herein, provides a high intensity, highly directional coherent spectrum of electromagnetic radiation wavelengths within a range of about 400 to about 2500 nm, that results from interaction of a pulsed laser and multiple non-linear processes to cause extensive spectral broadening.

Even in view of the state of the art, there remains need for application of improved sources of electromagnetic radiation and detector systems in reflectometer, spectrophotometer, ellipsometer, and polarimeter systems. Further, there remains need for additional systems directed to optimizing application of a plurality of detectors and/or wavelength dispersing elements which are arranged sequentially, and wherein each follow-on wavelength dispersing element receives a reflected altered spectral content reflected beam of electromagnetic radiation from a preceding wavelength dispersing element, and wherein each wavelength dispersing element produces at least one + or − spectrum of dispersed wavelengths which are directed toward a related detector.

DISCLOSURE OF THE INVENTION

The present invention is sample investigation system selected from the group consisting of:
a reflectometer;
a spectrophotometer;
an ellipsometer; and
a polarimeter;
comprising:
a) a source of a spectroscopic beam of electromagnetic radiation;
b) a stage for supporting a sample;
c) a detector system for monitoring electromagnetic radiation.

Said system being distinguished in that said source of a spectroscopic beam of electromagnetic radiation is super continuum laser that provides a high intensity, highly directional coherent spectrum of electromagnetic radiation wavelengths within a range of about 400 to about 2500 nm, that results from interaction of a pulsed laser and multiple non-linear processes to cause extensive spectral broadening. (Note High Intensity is to be interpreted to mean an intensity which is about thirty times or more times that of typical sources of electromagnetic radiation applied in Ellipsometer and the like systems). (Note, a Present Invention system wavelength range can be limited to between greater than 1000, to about 2500 nm).

In use, the preferred embodiment provides that said source of a spectroscopic beam of electromagnetic radiation directs a beam provided thereby to a sample placed on said stage for supporting a sample, at an oblique angle thereto. Further, the preferred embodiment does not involve said beam passing through a combination beam splitter and objective lens before interacting with said sample, as is the case in the Pandev 408 reference identified in the Background Section. Note, Pandev 408 is the only reference known to even remotely suggest application of a Super Continuum Laser in a reflectometer, spectrophotometer, ellipsometer or a polarimeter.

Said sample investigation system further comprises a speckle reducer in the form of a selection from the group consisting of:
a beam diffuser;
a fly's-eye beam homogenizer;
a rotating beam diffuser;
a piezoelectric electric crystal driven beam diffuser;
an electronic means to shorten temporal coherence length.
It is noted that speckle reducers serve to reduce wild swings in intensity of electromagnetic radiation as a function of position in a beam resulting from interference effects between different coherent wavelengths in said extensively broadened spectrum.

Said sample investigation system can further comprise a polarization state generator between said source of a beam of electromagnetic radiation and said stage for supporting a sample, and a polarization state analyzer between said stage for supporting a sample and said detector, and the system is an ellipsometer or polarimeter.

Further, said sample investigation system can further comprise a compensator in the polarization state generator and/or said polarization store detector, and the system is polarimeter.

Said detector system can further comprise means for producing a plurality of separate wavelength ranges from a spectroscopic beam incident thereupon, said system comprising a sequence of at least two elements, each thereof being selected from the group consisting of:
a grating which when presented with an incident spectroscopic beam of electromagnetic radiation produces a spectrum of diffracted dispersed wavelengths and simultaneous therewith an altered spectral content reflected beam of electromagnetic radiation;
a combination dichroic beam splitter-prism which when presented with a spectroscopic beam of electromagnetic radiation produces a spectrum of dispersed wavelengths that transmit through and exit from said prism, and simultaneous therewith an altered spectral content reflected beam of electromagnetic radiation.

In use a spectroscopic beam of electromagnetic radiation from said source thereof is caused to interact with a sample placed on said stage, and then impinge onto a first selected element such that a spectrum of dispersed wavelengths is produced and directed toward a first detector, simultaneous with production of a reflected altered spectral content reflected beam of electromagnetic radiation which is directed to impinge on a second selected element which likewise produces a spectrum of dispersed wavelengths which are directed toward a second detector.

The reflected altered spectral content reflected beam of electromagnetic radiation can be directed to impinge on a beam splitter that directs at least some of said beam onto a third selected element which produces a spectrum of dispersed wavelengths that are directed into a third detector, while continuing to direct at least some of said altered spectral content beam toward said second selected element which continues to direct the limited range spectrum of dispersed wavelengths produced thereby toward said second detector.

Said detector system can comprise at least one selection from the group consisting of:
at least one of said first and second selected elements is/are designed to optimally structure the range of wavelengths exiting therefrom;
at least one of said first and second detectors is/are designed to optimally detect the range of wavelengths input thereinto by said first and second selected elements respectively;
is functionally enabled.

Said detector system can further comprise more than two selected elements, and in which the reflected electromagnetic beam produced by the second selected element is directed toward at least one selection from the group consisting of:
a dichroic beam splitter and then therefrom impinge onto a third selected element;
directly impinge onto a third selected element;
at least one reflector and then a dichroic beam splitter and then therefrom impinge onto a third selected element; and at least one reflector and then impinge onto a third selected element.

Said detector system can provide that the third selected element, upon receiving said reflected beam of electromagnetic radiation produces a spectrum of dispersed wavelengths which are directed toward a third detector.

Said detector system can provide that at least one selection from the group consisting of:
said third selected element is designed to optimally structure the range of wavelengths exiting therefrom;
said third detector is designed to optimally detect the range of wavelengths input thereinto by said first and second selected elements respectively;
is enabled.

Said detector system can provide that a forth element is selected and in which the reflected electromagnetic beam produced by the third selected element or which exits a present dichroic beam splitter associated with said second selected element, is directed toward at least one selection from the group consisting of:
a dichroic beam splitter and then therefrom impinge onto a forth selected element;
directly impinge onto a forth selected element;
at least one reflector and then a dichroic beam splitter and then therefrom impinge onto a forth selected element; and
at least one reflector and then impinge onto a forth selected element.

Said detector system can provide that the forth selected element, upon receiving said reflected beam of electromagnetic radiation produces a spectrum of dispersed wavelengths which are directed toward a forth detector.

Said detector system can provide that at least one selection from the group consisting of:
said forth selected element is designed to optimally structure the range of wavelengths exiting therefrom;
said forth detector is designed to optimally detect the range of wavelengths input thereinto by said first and second selected elements respectively;
is enabled.

Said detector system can specifically involve a beam of spectroscopic electromagnetic radiation from said sample that is caused to impinge onto a grating or a combination dichroic beam splitter-prism which produces said spectrum of diffracted dispersed wavelengths, which spectrum is directed to enter a detector; and simultaneously produces said altered spectral content reflected beam of electromagnetic radiation which is directed to interact with a dichroic beam splitter that causes said altered spectral content reflected beam of electromagnetic radiation to split into two beams, both of which are directed to separate selections from the group consisting of:
a grating which when presented with an incident spectroscopic beam of electromagnetic radiation produces a spectrum of diffracted dispersed wavelengths and simultaneous therewith an altered spectral content reflected beam of electromagnetic radiation;
a combination dichroic beam splitter-prism which when presented with a spectroscopic beam of electromagnetic radiation produces a spectrum of wavelengths that transmit through and exit from said prism, and simultaneous therewith an altered spectral content reflected beam of electromagnetic radiation;
such that the spectrum of dispersed wavelengths that exit from a present grating or combination dichroic beam splitter-prism are each caused to enter separate detectors.

Said detector system can provide that the spectroscopic beam of electromagnetic radiation from said sample which is caused to impinge onto a first selected element such that a spectrum of dispersed wavelengths is produced and directed toward a first detector, simultaneous with production of an altered spectral content reflected beam of electromagnetic radiation which is directed to impinge on a second selected element which likewise produces a spectrum of dispersed wavelengths which are directed toward a second detector, is the output beam of an ellipsometer or polarimeter which exits the analyzer thereof.

Said detector system can specifically involve a beam of spectroscopic electromagnetic radiation from said sample that is caused to interact with a sequence of elements comprising:
a first grating and first and first detector, wherein the reflected beam exiting said first grating is a zero order beam and is directed to a second grating and second detector.

Said detector system can specifically involve a beam of spectroscopic electromagnetic radiation from said sample that is caused to interact with a sequence of elements comprising:
a first grating and first detector, wherein the reflected beam exiting said first grating is a zero order beam and is directed to a first combination dichroic beam splitter-prism and second detector.

Said detector system can specifically involve a beam of spectroscopic electromagnetic radiation from said sample that is caused to interact with a sequence of elements comprising:
a dichroic beam splitter which sends first and second ranges of dispersed wavelengths, which are substantially above and below a certain wavelength, respectively, each to a selection from the group consisting of:
a first grating and first detector, wherein the reflected beam exiting said first grating is a zero order beam and is directed to a second grating and second detector; and
a first grating and first detector, wherein the reflected beam exiting said first grating is a zero order beam and is directed to a first dichroic beam splitter-prism combination and second detector.

Said detector system can specifically involve a beam of spectroscopic electromagnetic radiation from said sample that is caused to interact with a sequence of elements comprising:
a first combination dichroic beam splitter-prism and first detector, and wherein the reflected beam reflecting from said first combination dichroic beam splitter-prism is directed to a first grating and second detector.

Said detector system can specifically involve a beam of spectroscopic electromagnetic radiation from said sample that is caused to interact with a sequence of elements comprising:
a first grating and first detector, wherein the reflected beam produced by said first grating is a zero order beam and is directed to a second grating and second detector, and in which the reflected beam produced by said second grating is a zero order beam directed to a third grating and third detector.

Said detector system can specifically involve a beam of spectroscopic electromagnetic radiation from said sample that is caused to interact with a sequence of elements comprising:
a first grating and first detector, wherein the reflected beam produced by said first grating is a zero order beam and is directed to a first combination dichroic beam splitter-prism and second detector, and in which the reflected beam reflected from said first combination dichroic beam splitter-prism is directed to a third grating and third detector via a dichroic beam splitter.

Said detector system can specifically involve a beam of spectroscopic electromagnetic radiation from said sample that is caused to interact with a sequence of elements comprising:
  a first grating and first detector, wherein the reflected beam produced by said first grating is a zero order beam and is directed to a second grating and second detector, and in which the reflected beam produced by said second grating is a zero order beam and is directed to a first dichroic beam splitter-prism combination and third detector.

Said detector system can specifically involve a beam of spectroscopic electromagnetic radiation from said sample that is caused to interact with a sequence of elements comprising:
  a first grating and first detector, wherein the reflected beam produced by said first grating is a zero order beam and is directed to a first combination dichroic beam splitter-prism and second detector, and in which the reflected beam reflected from said first combination dichroic beam splitter-prism is directed to a second dichroic beam splitter-prism combination and third detector via a beam splitter.

Said detector system can specifically involve a beam of spectroscopic electromagnetic radiation from said sample that is caused to interact with a sequence of elements comprising:
  a first combination dichroic beam splitter-prism and first detector, wherein the reflected beam reflected by said first combination dichroic beam splitter-prism is directed to a second grating and second detector, and in which the reflected beam produced by said second grating is a zero order beam and is directed to a third grating and third detector.

Said detector system can specifically involve a beam of spectroscopic electromagnetic radiation from said sample that is caused to interact with a sequence of elements comprising:
  a first combination dichroic beam splitter-prism and first detector, wherein the reflected beam reflected from said first combination dichroic beam splitter-prism is directed to a second dichroic beam splitter-prism combination and second detector, and in which the reflected beam reflected from said second combination dichroic beam splitter-prism is directed to a third grating and third detector via a dichroic beam splitter.

Said detector system can specifically involve a beam of spectroscopic electromagnetic radiation from said sample that is caused to interact with a sequence of elements comprising:
  a first combination dichroic beam splitter-prism and first detector, wherein the reflected beam reflected from said first combination dichroic beam splitter-prism is directed to a first grating and second detector, and in which the reflected beam produced by said second grating is a zero order beam and is directed to a second combination dichroic beam splitter-prism and third detector.

Said detector system can specifically involve a beam of spectroscopic electromagnetic radiation from said sample that is caused to interact with a sequence of elements comprising:
  a first combination dichroic beam splitter-prism and first detector, wherein the reflected beam reflected from said first combination dichroic beam splitter-prism is directed to a second combination dichroic beam splitter-prism and second detector, and in which the reflected beam reflected from said combination second dichroic beam splitter-prism is directed to a third combination dichroic beam splitter-prism and third detector via a beam splitter.

Said detector system can involve a spectrum of dispersed diffracted wavelengths are produced by a grating is a + or − order spectrum.

A present invention method comprises the steps of:
  a) providing a sample investigation system selected from the group consisting of:
    a reflectometer;
    a spectrophotometer;
    an ellipsometer; and
    a polarimeter;
  comprising:
    a) a source of a beam of a spectroscopic beam of electromagnetic radiation;
    b) a stage for supporting a sample; and
    c) a detector system for monitoring electromagnetic radiation.

Said system is distinguished in that said source of a spectroscopic beam of electromagnetic radiation is a super continuum laser that provides a high intensity, highly directional coherent spectrum of electromagnetic radiation wavelengths within a range of about 400 to about 2500 nm, that results from interaction of a pulsed laser and multiple non-linear processes to cause extensive spectral broadening.

Said system is further distinguished in that it further comprises a speckle diminisher in the form of a selection from the group consisting of:
  a beam diffuser;
  a fly's-eye beam homogenizer;
  a rotating beam diffuser;
  a piezoelectric electric crystal driven beam diffuser;
  an electronic means to shorten temporal coherence length.

In use said speckle reducer serves to reduce wild swings in intensity of electromagnetic radiation as a function of position within a beam resulting from interference effects between different coherent wavelengths in said extensively broadened spectrum.

Said system is further distinguished in that said detector system comprises means for producing a plurality of separate wavelength ranges from a spectroscopic beam incident thereupon, said system comprising a sequence of at least two elements, each thereof being selected from the group consisting of:
  a grating which when presented with an incident spectroscopic beam of electromagnetic radiation produces a spectrum of diffracted dispersed wavelengths and simultaneous therewith an altered spectral content reflected beam of electromagnetic radiation;
  a combination dichroic beam splitter-prism which when presented with a spectroscopic beam of electromagnetic radiation produces a spectrum of dispersed wavelengths that transmit through and exit from said prism, and simultaneous therewith an altered spectral content reflected beam of electromagnetic radiation.

In use a spectroscopic beam of electromagnetic radiation provided by said supercontinuum laser and speckle reducer is caused to interact with a sample placed upon said stage, and then impinge onto a first selected element such that a spectrum of dispersed wavelengths is produced and directed toward a first detector, simultaneous with production of a reflected altered spectral content reflected beam of electromagnetic radiation which is directed to impinge on a second selected element which likewise produces a spectrum of dispersed wavelengths which are directed toward a second detector.

(Note, the spectrum of dispersed diffracted wavelengths produced by a grating can be a + or − order spectrum).

Said method continues with:

b) causing a spectroscopic beam of speckle reduced electromagnetic radiation provided by said super continuum laser and speckle reducer to interact with a sample on said stage, then impinge onto a first selected element such that a spectrum of dispersed wavelengths is produced and directed toward a first detector, simultaneous with production of a reflected altered spectral content reflected beam of electromagnetic radiation which is directed to impinge on a second selected element which likewise produces a spectrum of dispersed wavelengths which are directed toward a second detector.

Said method can further comprise providing a beam splitter between said first and second selected elements which each produce a spectrum of dispersed wavelengths which are directed toward a second detector; and c) causing the reflected altered spectral content reflected beam of electromagnetic radiation which is directed to impinge on a beam splitter so that it directs at least some of said beam into onto a third selected element which produces a spectrum of dispersed wavelengths and directs it into a third detector, while also directing at least some of said beam toward said second selected element which continues to direct the spectrum of dispersed wavelengths produced thereby toward said second detector.

(In the foregoing, it is noted that the altered spectral content reflected beam of electromagnetic radiation is typically selected to be a zero order beam that reflects from a grating, and a beam that reflects from a dichroic beam splitter in a combination dichroic beam splitter-prism combination).

The present invention will be better understood by reference to the Detailed Description of this Specification in conjunction with the Drawings.

BRIEF DESCRIPTION OF THE DRAWINGS

FIG. 3a' shows the situation wherein a Reflected (RB) beam is reflected from dichroic beam splitter-prism (DBS-PR) combination at a surface thereof on which is present a Coating, to give it the Dichroic property. Note that a spectrum of at least a + or − order spectrum exits the Prism (P).

FIGS. 7a and 7b show, respectively, typical Intensity vs. position in a beam for a beam of electromagnetic radiation provided by a supercontinuum laser source over a range of about 400-2500 nm, and the same results when a Speckle Reducer is applied to the plot of FIG. 7a.

FIGS. 10a-10d show various Speckle Reducers.

DETAILED DESCRIPTION

To begin, it must be understood that the present invention is comprised of a combination of at least two fundamentally different sub-inventions, these being:

systems of detectors that can be optimized for use in various ranges of electromagnetic radiation, and use of a supercontinuum laser for providing a beam of coherent electromagnetic radiation over a wavelength range of about 400-2500 nm.

The present invention preferably is also be considered to include a third sub-invention category, that being:

application of a speckle reducer to effectively provide a more consistent Intensity vs. Position in a beam of electromagnetic radiation derived from the supercontinuum laser output.

In various combinations, said present invention is believed to be new, novel and non-obvious.

As the Intensity of a beam of electromagnetic radiation from a supercontinuum laser is generally much higher over a very large range of wavelengths, than is the case from other sources of electromagnetic radiation conventionally used in ellipsometric and the like applications, and as the present invention system of detectors can provide optimized detection of electromagnetic radiation in specific ranges of wavelengths, the present invention provides utility in the form of allowing a user thereof to conveniently investigate samples over a very large range of wavelengths without the necessity of reconfiguring the system with different sources and detectors of electromagnetic radiation.

Figure 1:
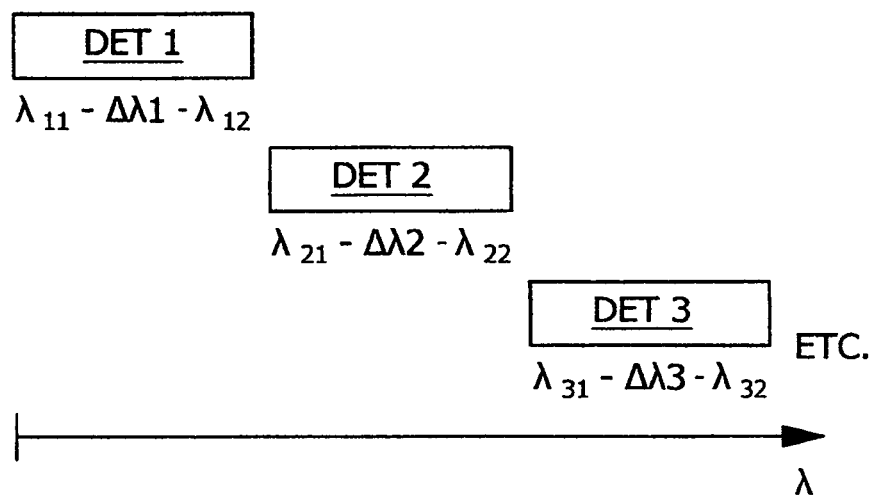
FIG. 1 demonstrates a number of wavelength ranges in which various multi-channel detectors (DET1) (DET2) (DET3) are designed to handle optimally.

Turning now to FIG. 1, there are demonstrated a number of wavelength ranges in which various multi-channel detectors (DET1) (DET2) (DET3) are designed to handle optimally. Many additional wavelength ranges could be shown similarly as well, such as a (4) as shown in FIG. 2.

Figure 2:
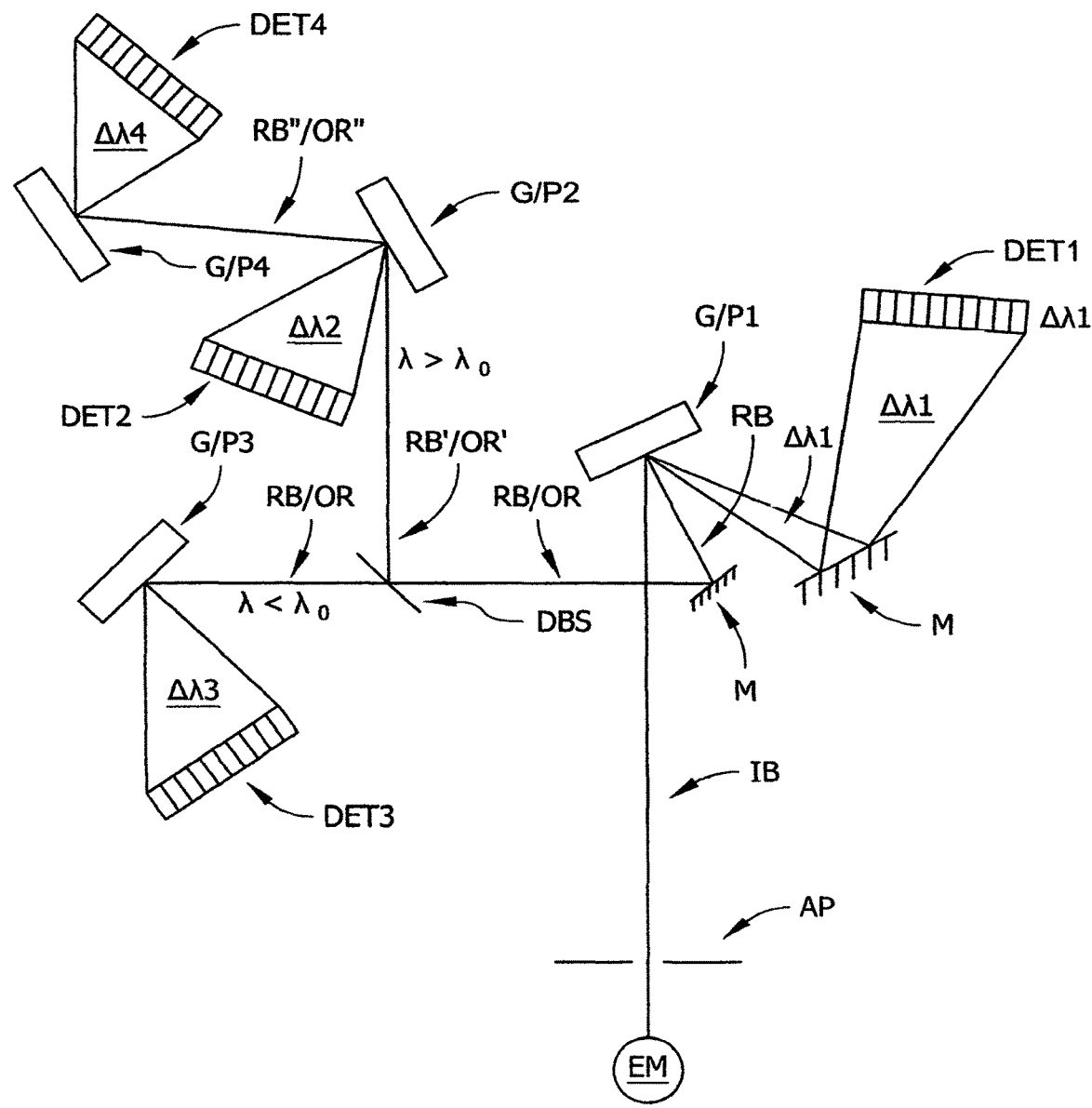
FIG. 2 shows some present invention combinations of multiple Gratings (G) and/or Dichroic Beam Splitter-Prism Combinations (DBSP), (generically represented as (G/P)), as examples that each produce at least one + or − order spectrum of wavelengths as well as a relatively more energetic Reflected Beam, (eg. Zero Order (ZO) in the case of a Grating), beam of electromagnetic radiation, which is directed to a follow-on Grating (G).

FIG. 2 shows combinations multiple Gratings (G) and/or Dichroic Beam Splitter-Prism Combinations (DBSP), (represented G/P "_" in FIG. 2), that each produce at least one + or − order spectrum (λ) of wavelengths, as well as an altered spectral content Reflected (RB/OR) beam of electromagnetic radiation, (eg. a Zero Order (OR) beam as in the case of a Grating (G) or a functionally similar Reflected Beam (RB) in the case of a Dichroic Beam Splitter-Prism Combinations (DBSP). See Reflected Beam (RB) in FIG. 3a' as regards a combination dichroic beam splitter-prism (DBSP) and Zero Order (OR) Beam in FIG. 3a. (Note, the terminology Zero Order (ZO) is not correct in a critical sense where a Dichroic Beam Splitter-Prism Combinations (DBSP), rather than a Grating (G) is applied, even though the results provided are functionally similar). FIG. 2 is a relevant example of a Present Invention System wherein a Source (EM) of a Beam of electromagnetic radiation (IB) is shown to provide electromagnetic radiation through an Aperture (AP), and impinge on (G/P1). Exiting (G/P1) is a First Range of a + or −, typically first Order spectrum of wavelengths (λ) which proceed, via reflection from a Mirror (M) as shown to Detector (DET1). Also shown is Reflected beam (RB) which reflects from another Mirror (M) and encounters a Dichroic Beam Splitter (DBS), which (DBS) directs a first amount of the entering beam to (G/P3) which disperses it into a range of wavelengths (λ) which are directed into Detector (DET3). A second amount of the Beam entering the (DBS) exits toward (G/P2) which provides a dispersed range of wavelengths (λ) that are directed into Detector (DET2), and also directs a Reflected Beam (RB"/OR") to (G/P4) which provides a dispersed range of wavelengths (λ) to Detector (DET4).

Figure 3A:
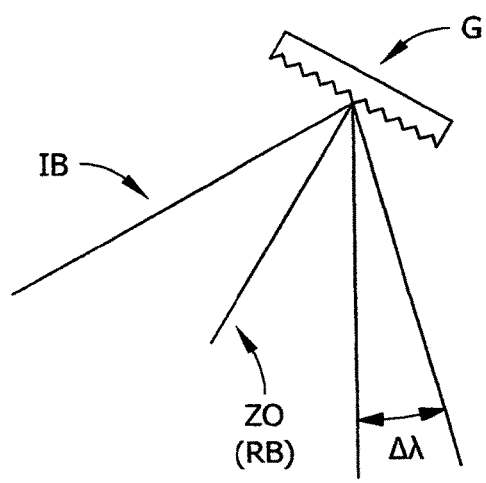
FIG. 3a shows a grating (G) that reflects an incoming beam (IB) of electromagnetism, and provides a spectrum of wavelengths ( ) in an order thereof, (eg. the first + Order), along with a Zero Order (ZO).
Figure 3A:
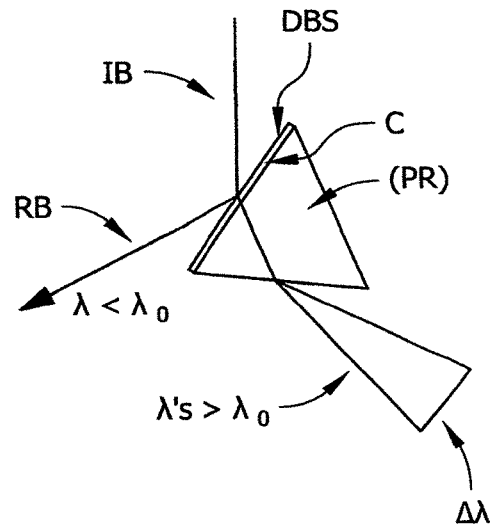

FIG. 3a demonstrates a Grating (G) wherein an Input Beam (IB) of electromagnetic radiation is impinged thereonto, with the result that at least one +/− Order Spectrum of wavelengths is produced along with a Zero Order (ZO) beam.

FIG. 3a' shows the situation wherein a Reflected (RB) beam is reflected from Dichroic Beam Splitter-Prism (DBS-PR) combination at a surface thereof on which is present a Coating, to give it the Dichroic property. Note that a spectrum of at least a + or − order spectrum exits the Prism (P). A coating (C) is indicated as present on the surface onto which the Input Beam impinges, and serves to form the Dichroic Beam Splitter (DBS).

For insight, Dichroic refers to different properties, eg. reflection/transmission of electromagnetic radiation, based on wavelength.

It is to be understood that the designations of (G/P_) in FIG. 2 is to be interpreted as possibly being either of the systems in FIGS. 3a and 3a'.

Figure 4:
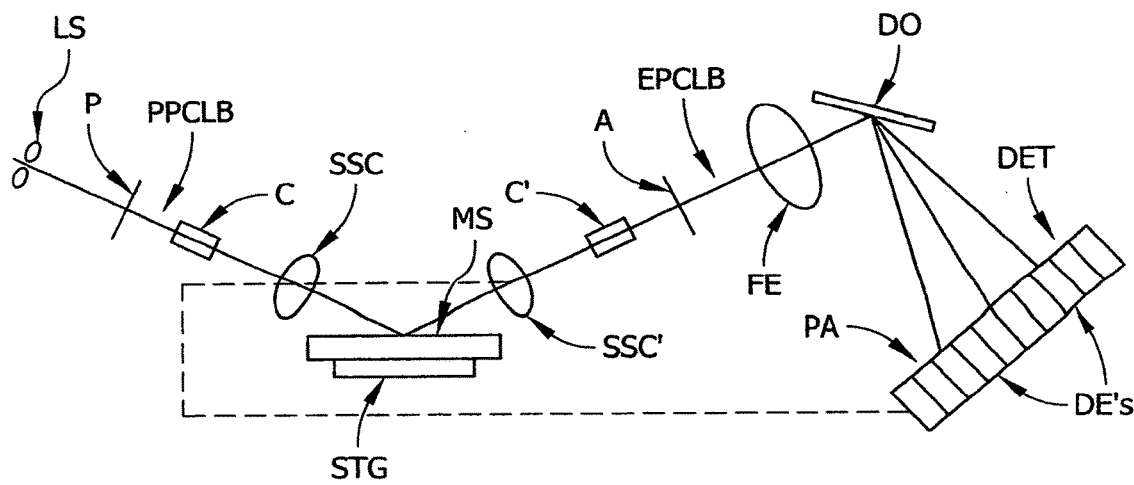
FIG. 4 demonstrates an ellipsometer system, in which the present invention finds very relevant application.

FIG. 4, (which is FIG. 2 taken from U.S. Pat. No. 7,345,762 to Liphardt et al.), is included to demonstrate an ellipsometer system, in which ell-ipsometer and polarimeter and the like systems the present invention finds very relevant application. When so applied the beam exiting the ellipsometer polarization state analyzer, (ie. (EPCLB) in said FIG. 4), is beneficially considered as being the beam (IB) shown in accompanying FIG. 2. Roughly, Grating (Gi) in FIG. 2 corresponds to Dispersive Element (ie. Grating), (DO) in said FIG. 4. Note that FIG. 4 shows an ellipsometer Source (LS) which provides an ellipsometer beam (PPCLB) which has been polarized by interaction with the shown Polarizer (P). Said beam (PPCLB) is then caused to interact with a shown Sample (MS), which is indicated can be a focused beam at that point. A beam reflected from said Sample (MS) can be re-collimated, and then pass through an Analyzer (A) and emerge as beam (EPCLB), before being focused by (FE) onto a Dispersive Element, (eg. a Grating) (DO), which (DO) serves to disperse wavelengths into a Multi-element Detector (PA). One or two Compensators (C) can also be present as shown in the Polarization State Generator or Analyzer or the system associated with the Polarizer and Analyzer respectively. Again, for correspondence, Dispersive Element (DO) is roughly equivalent to Grating (G1) in FIG. 2. Also shown is indication that the Focusing (SSC) and Recollimating (SSC') lenses can be controlled as to position to optimize intended effects.

Figure 5:
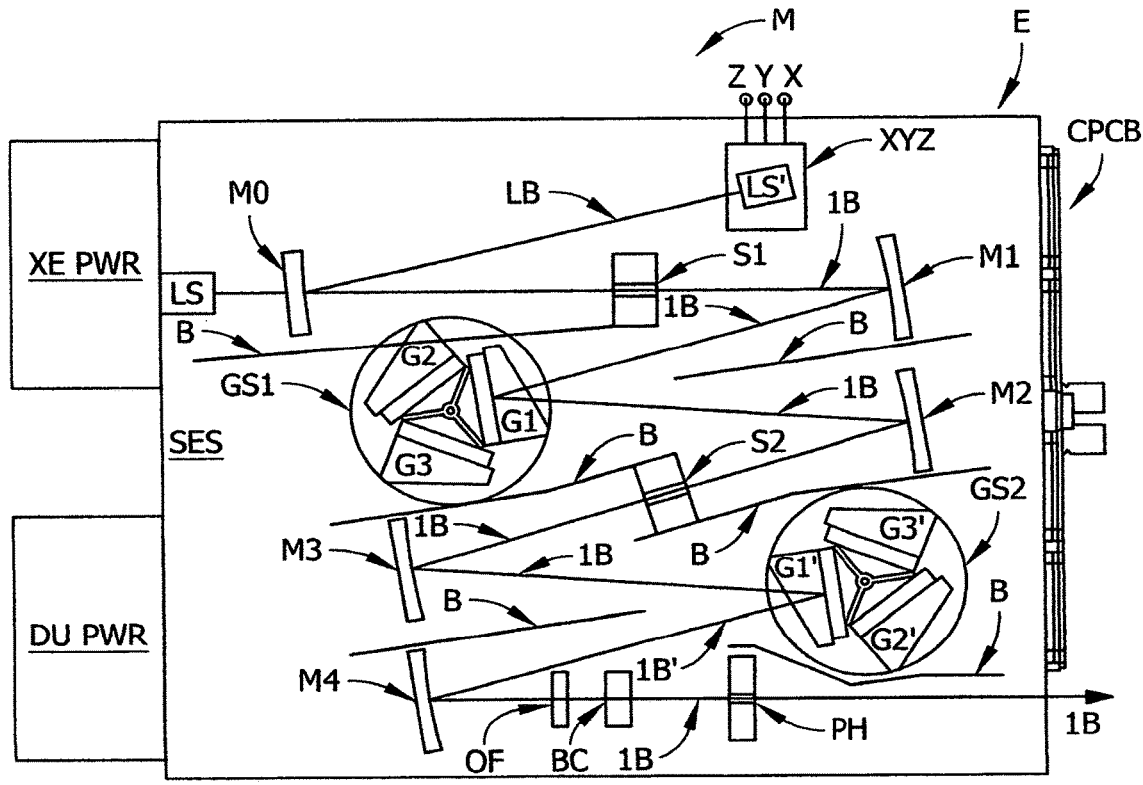
FIG. 5 shows the use of sequential follow-on Gratings which electromagnetic radiation sequentially caused to encounter.

FIG. 5, (from FIG. 9 in U.S. Pat. No. 7,345,762), is included to show the use of sequential follow-on Gratings (eg. G1 and G1') to arrive at a desired wavelength in a spectrometer system.

Figure 6:
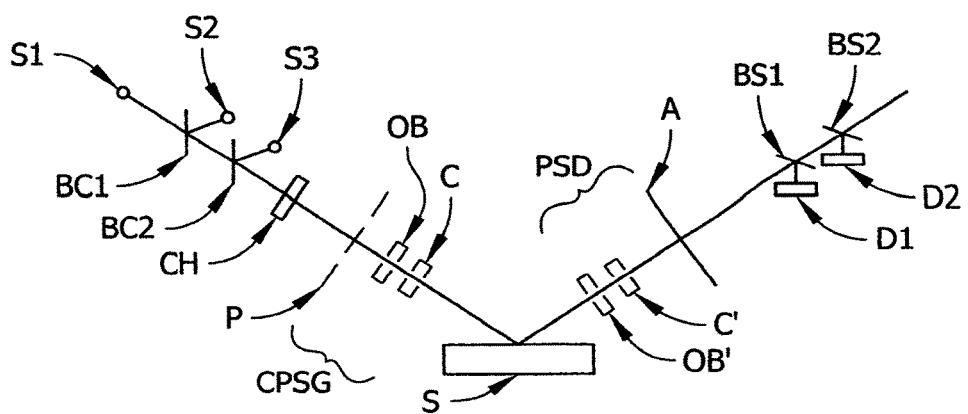
FIG. 6 shows the use of beam splitters to direct portions of beams into different detectors which can be optimized to respond to different wavelength ranges.

FIG. 6, (taken from FIG. 1a in U.S. Pat. No. 8,169,611), is included to show the use of beam splitters (B1, and B2) to direct portions of beams into different detectors (D1 and D2) which can be optimized to respond to different wavelength ranges. See U.S. Pat. Nos. 7,345,762 and 8,169,611 for more clarification. Said Patents however, do not suggest the present invention directing a Reflected altered spectral content Beam to follow-on beam dispersing elements. FIG. 6 also shows the use of beam splitters to direct portions of beams into different detectors which can be optimized to respond to different wavelength ranges.

The +/− orders shown in the Drawings can be described generally as being wavelength ranges that are produced when a grating is presented with an incident spectroscopic beam of electromagnetic radiation and in response produces a spectrum of diffracted dispersed wavelengths, and simultaneous with an altered spectral content reflected beam of electromagnetic radiation, typically a Zero-Order beam.

Figure 7A:
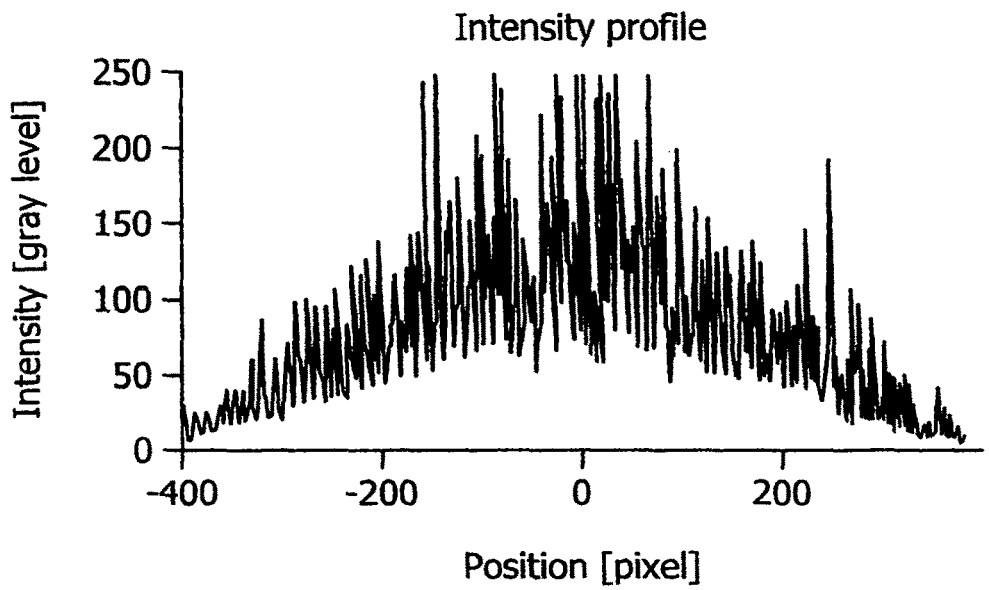

Continuing, FIG. 7a shows a typical Intensity vs. Position within a Beam Cross-section for a beam of electromagnetic radiation provided by a supercontinuum laser source over a range of about 400-2500 nm. Note in particular that effects of interactions between coherent components thereof leads to a very inconsistent Intensity plot. It is noted that Speckle can lead to Wavelength instability.

Figure 7B:
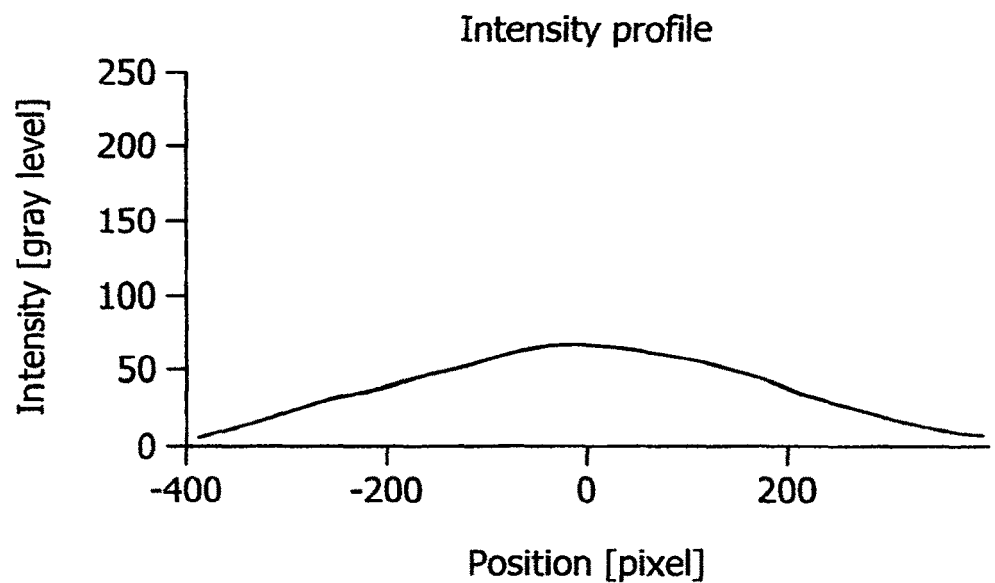

FIG. 7b shows that application of a "Speckle Reducer" to the beam Intensity profile in FIG. 6 allows a much more stable beam intensity vs. position in a beam profile to be achieved. This much more stable intensity profile is well suited to application in metrology systems such as ellipsometers, polarimeters, reflectometers and reflectometers. It is believed that use of a Supercontinuum Laser Source and Speckle Reducer as described in this Specification is new and novel, particularly in combination with the also described system of Detectors. As mentioned earlier in this Specification, a coherent source leads to interference effects, the present system comprises a speckle diminisher in the form of a selection from the group consisting of:
  a beam diffuser;
  a fly's-eye beam homogenizer;
  a rotating beam diffuser;
  a piezoelectric electric crystal driven beam diffuser;
  an electronic means to shorten temporal coherence length.
    to effectively remove wide changes in intensity very small wavelength ranges, (ie. speckle).

Figure 8A:
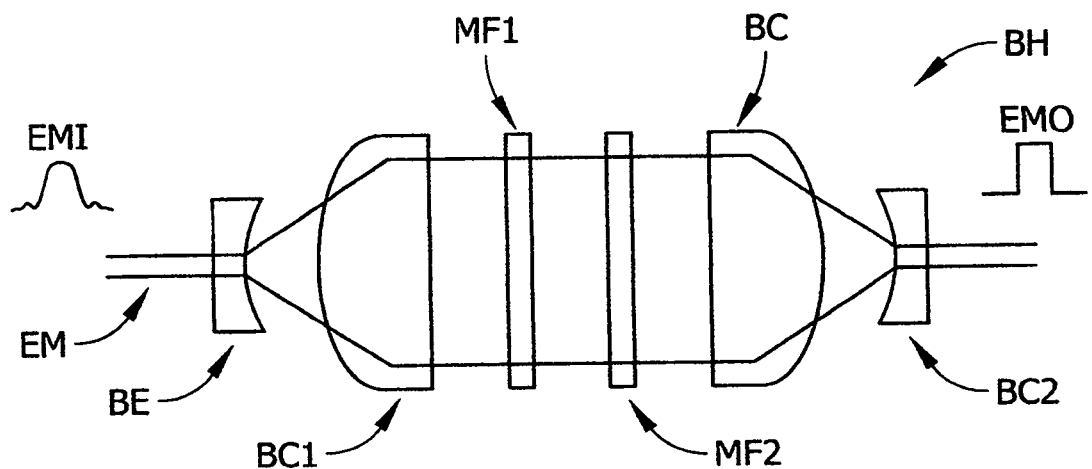
FIGS. 8a-8a''' show a Fly's Eye approach to reducing Speckle.
Figure 8A:
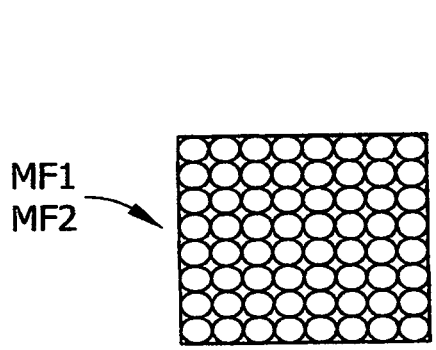
Figure 8A:
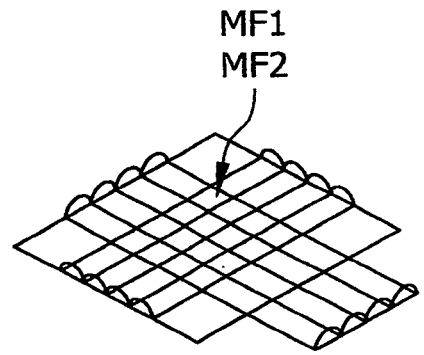
Figure 8A:
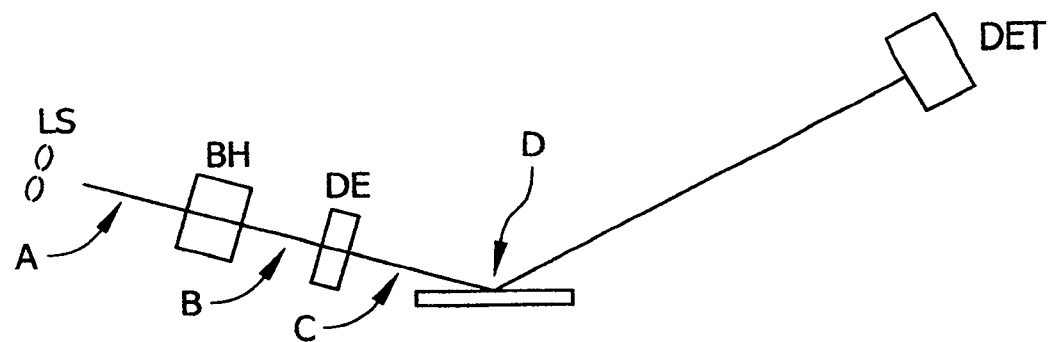

FIGS. 8a-8a''' show a Fly's Eye approach to reducing Speckle. Note that in FIG. 8a shows that input electromagnetic radiation shown as (EM1), which is of a very uneven intensity but can be transformed into output electromagnetic radiation shown as (EMO), which is of a very even intensity. The system consists of a Beam Expander (BE), a Beam Collimator (BC1), two Fly's Eye lenses (MF1) (MF2), a second Beam Collimator (BC2) applied to focus the Collimated beam exiting (MF2), and a Second Beam Collimator (BC2) which re-collimates the beam presented to it. The energy content of (EM1) has been distributed uniformly by the actions of the Fly's Eye lenses (MF1) and (MF2) as indicated by (EMO). FIGS. 8*a*' and 8*a*" show typical Fly's Eye lens construction. FIG. 8*a*'" is included to indicate how the system of FIG. 8*a* (BH) can be applied in an Ellipsometer system. At "A" the entering beam from Source (LS) is as shown as (EM1), and "B" the beam energy is distributed as is shown by (EMO), and a Polarization Element (DE) can be applied prior to said beam interacting with Sample (and location (D), with a Detector positioned to monitor a reflected beam from said Sample at location (D) thereon.

Figure 9A:
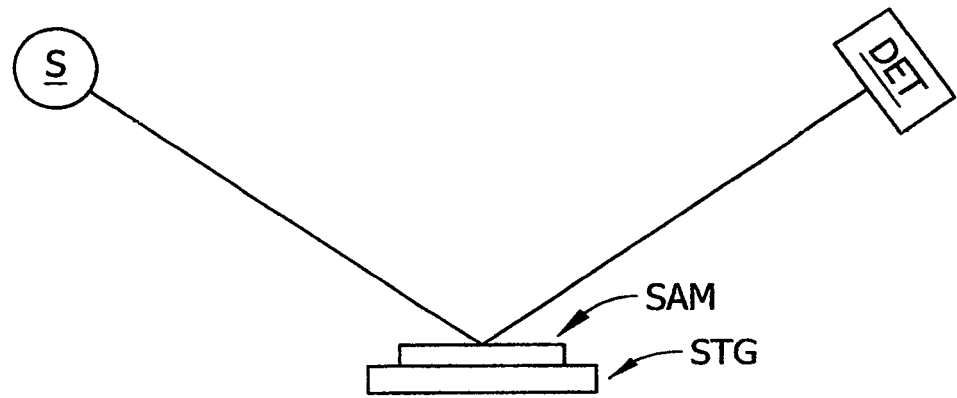
FIGS. 9a and 9b are included to show a basic reflectometer or spectrophotometer system, and a basic ellipsometer of polarimeter system, respectively.

FIG. 9*a* is included to show a basic reflectometer or spectrophotometer system comprising:
 a) a source (S) of a beam of electromagnetic radiation;
 b) a stage (STG) for supporting a sample (SAM);
 c) a detector system (DET) of electromagnetism;
said system being distinguished, in the present invention, in that said source (S) of a spectroscopic beam of electromagnetic radiation is a super continuum laser that provides an output spectrum as shown FIGS. 7*a* and preferably 7b. That is, a primary distinguishing aspect of the present invention is the use of a high intensity, highly directional super continuum laser to provide electromagnetic radiation. As described earlier with respect to FIG. 2, another aspect of the present invention involves use of detector systems that provide wavelengths of various ranges to detectors that are well suited to detecting said wavelengths.

Figure 9B:
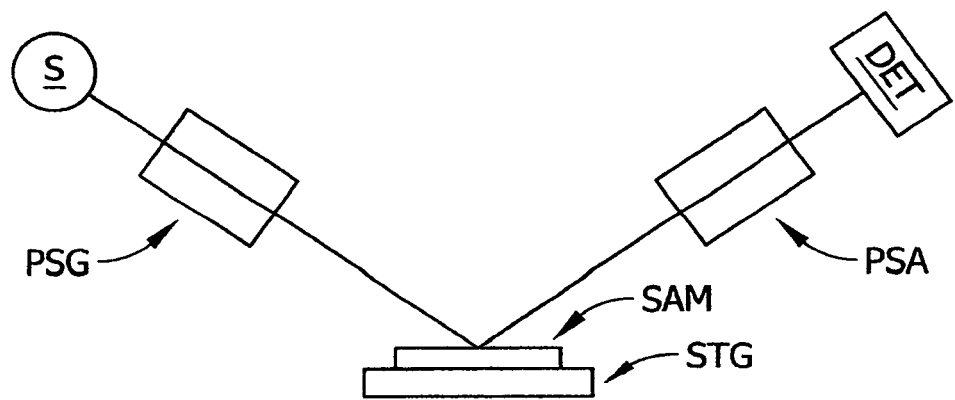

FIG. 9*b* shows the elements of FIG. 9*a* with polarization state generator (PSG) and polarization state analyzer (PSA) added, to effect an ellipsometer or polarimeter system.

FIGS. 10*a*-10*d* show various speckle Reducers. FIG. 10*a* shows a Beam Diffuser Plate with an Input Beam (BI) entering thereinto, and exiting as Diffused Beam (DBO) components. FIG. 10*b* shows a Fly's Eye lens (FE) which causes a similar effect as does the Beam Diffuser in FIG. 10*a* when a beam is passed therethrough. FIG. 10*c* shows the Beam Diffuser (BD) of FIG. 10*a* attached to a Motor (M) that causes it to rotate in use. An Input Beam (B) is again passed therethrough as shown, and emerges as a Diffused Beam (DBO). FIG. 10*d* shows a Beam Diffuser (BD) Plate, again as in FIG. 10*a*, attached to Piezoelectric Drivers (PZ) that are applied to cause the Beam Diffuser (BD) to vibrate vertically and/or horizontally in use. The Fly's Eye (FE) Lens can also be used in the configurations of FIGS. 10*c* and 10*d*.

Figure 11:
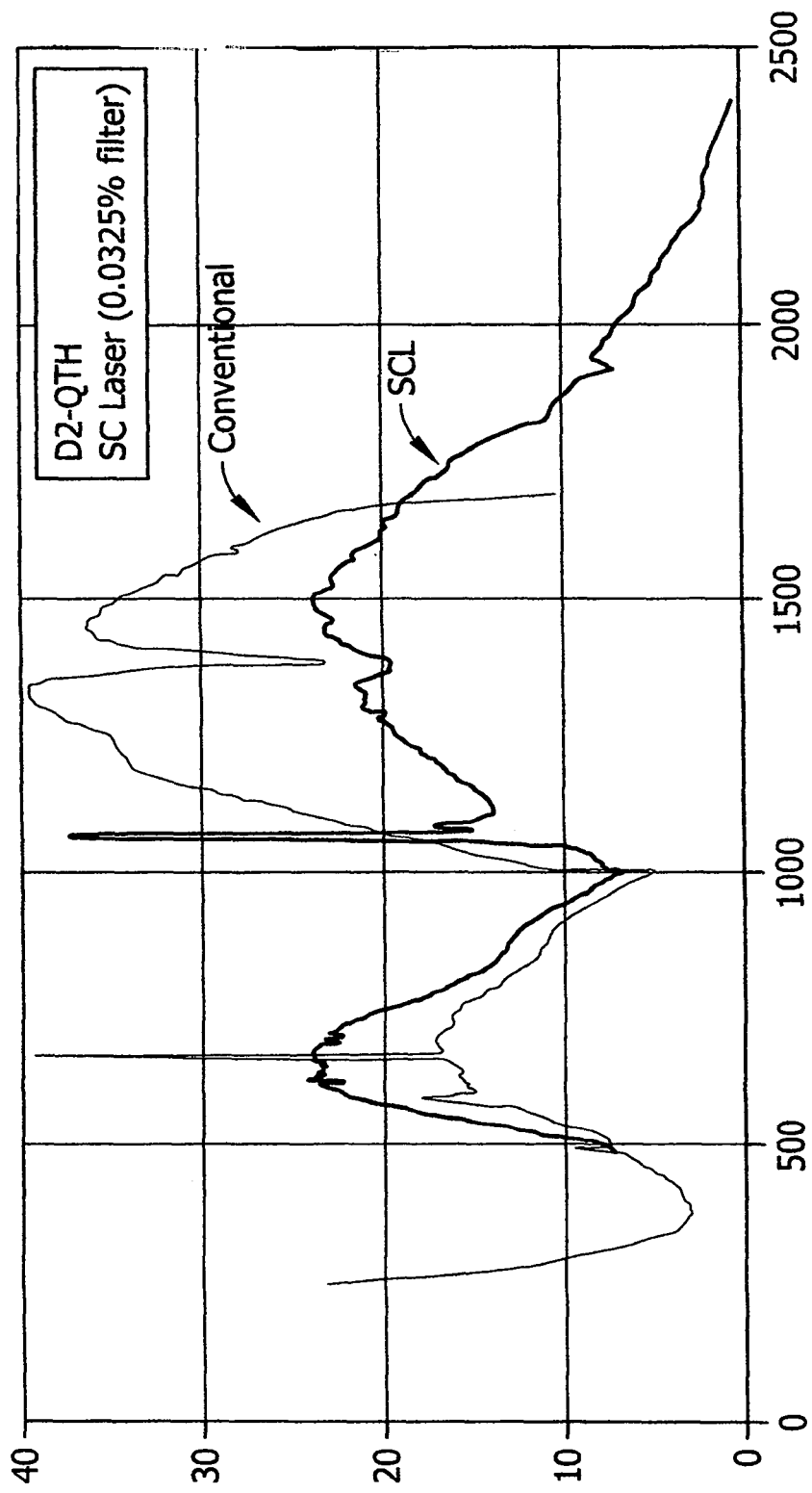
FIG. 11 is included to show a typical Inventor generated Intensity vs. Wavelength result from a super continuum laser, as compared to a typical conventional source of electromagnetic radiation intensity vs. Wavelength.

FIG. 11 is included to show a typical Inventor of the present invention generated Intensity vs. Wavelength result from a super continuum laser when a 0.0325% neutral density filter is present in the path of the super continuum laser beam, as compared to a conventional source of electromagnetic radiation intensity vs. Wavelength. Note, the Super Continuum Laser intensity is very much greater than that of the Conventional Source Spectrum, (shown as about thirty times greater), and to compare their wavelength spectrum characteristics it was necessary that it be greatly attenuated by a 0.0325 neutral density filter.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A sample investigation system selected from the group consisting of:
 a reflectometer;
 a spectrophotometer;
 an ellipsometer; and
 a polarimeter;
comprising:
 a) a source of a spectroscopic beam of electromagnetic radiation;
 b) a stage for supporting a sample; and
 c) a detector system for monitoring electromagnetic radiation;
said system being configured such that a beam of electromagnetic radiation produced by said source is directed to interact with a sample placed on said stage for supporting a sample so that it interacts with said sample and then proceeds, as the beam of electromagnetic radiation, into said detector;
said system being distinguished in that:
said source of a spectroscopic beam of electromagnetic radiation is a super continuum laser that provides a high intensity, highly directional coherent spectrum of electromagnetic radiation wavelengths within a range of about 400 to about 2500 nm, that results from interaction of a pulsed laser and multiple non-linear processes to cause extensive spectral broadening;
and in that:
in use, said source of a spectroscopic beam of electromagnetic radiation directs a beam provided thereby to a sample placed on said stage for supporting a sample, at an angle thereto;
said detector system further comprising means for producing a plurality of separate wavelength ranges from a spectroscopic beam incident thereupon, said system comprising a sequence of at least two elements, each thereof being selected from the group consisting of:
 a grating which when presented with an incident spectroscopic beam of electromagnetic radiation produces a spectrum of diffracted dispersed wavelengths and simultaneous therewith an altered spectral content reflected beam of electromagnetic radiation; and
 a combination dichroic beam splitter-prism which when presented with a spectroscopic beam of electromagnetic radiation produces a spectrum of dispersed wavelengths that transmit through and exit from said prism, and simultaneous therewith an altered spectral content reflected beam of electromagnetic radiation;
such that in use a spectroscopic beam of electromagnetic radiation from said source thereof is caused to interact with a sample placed on said stage, and then impinge onto a first selected element such that a spectrum of dispersed wavelengths is produced and directed toward a first detector, simultaneous with production of a reflected altered spectral content reflected beam of electromagnetic radiation which is directed to impinge on a second selected element which likewise produces a spectrum of dispersed wavelengths which are directed toward a second detector.

2. A system as in claim 1, in which said sample investigation system further comprises a speckle reducer in the form of a selection from the group consisting of:
 a beam diffuser;
 a fly's-eye beam homogenizer;
 a rotating beam diffuser;
 a piezoelectric electric crystal driven beam diffuser;
 an electronic means to shorten temporal coherence length;
said speckle reducer serving to reduce wild swings in intensity of electromagnetic radiation as a function of time and position in a beam, resulting from interference effects between different coherent wavelengths in said extensively broadened spectrum.

3. A system as in claim 2, in which said sample investigation system comprises a speckle reducer in the form of a beam diffuser.

4. A system as in claim 2, in which said sample investigation system comprises a speckle reducer in the form of a fly's-eye beam homogenizer.

5. A system as in claim 2, in which said sample investigation system comprises a speckle reducer in the form of a rotating beam diffuser.

6. A system as in claim 2, in which said sample investigation system comprises a speckle reducer in the form of a piezoelectric electric crystal driven beam diffuser.

7. A system as in claim 2, in which said sample investigation system comprises a speckle reducer in the form of an electronic means to shorten temporal coherence length.

8. A system as in claim 1, in which said sample investigation system further comprises a polarization state generator between said source of a beam of electromagnetic radiation and said stage for supporting a sample, and a polarization state analyzer between said stage for supporting a sample and said detector, and the system is an ellipsometer or polarimeter.

9. A system as in claim 8, in which said sample investigation system further comprises a compensator in the polarization state generator and/or said polarization store detector, and the system is polarimeter.

10. A system as in claim 1, in which the reflected altered spectral content reflected beam of electromagnetic radiation is directed to impinge on a beam splitter that directs at least some of said beam onto a third selected element which produces a spectrum of dispersed wavelengths that are directed into a third detector, while continuing to direct at least some of said altered spectral content beam toward said second selected element which continues to direct the limited range spectrum of dispersed wavelengths produced thereby toward said second detector.

11. A system as in claim 1, in which at least one selection from the group consisting of:
at least one of said first and second selected elements is/are designed to optimally structure the range of wavelengths exiting therefrom;
at least one of said first and second detectors is/are designed to optimally detect the range of wavelengths input thereinto by said first and second selected elements respectively;
is functionally enabled.

12. A system as in claim 1 which further comprises more than two selected elements, and in which the reflected electromagnetic beam produced by the second selected element is directed toward at least one selection from the group consisting of:
a dichroic beam splitter and then therefrom impinge onto a third selected element;
directly impinge onto a third selected element;
at least one reflector and then a dichroic beam splitter and then therefrom impinge onto a third selected element; and
at least one reflector and then impinge onto a third selected element.

13. A system as in claim 12 in which the third selected element, upon receiving said reflected beam of electromagnetic radiation produces a spectrum of dispersed wavelengths which are directed toward a third detector.

14. A system as in claim 13, in which at least one selection from the group consisting of:
said third selected element is designed to optimally structure the range of wavelengths exiting therefrom;
said third detector is designed to optimally detect the range of wavelengths input thereinto by said first and second selected elements respectively;
is enabled.

15. A system as in claim 12 which a forth element is selected and in which the reflected electromagnetic beam produced by the third selected element or which exits a present dichroic beam splitter associated with said second selected element, is directed toward at least one selection from the group consisting of:
a dichroic beam splitter and then therefrom impinge onto a forth selected element;
directly impinge onto a forth selected element;
at least one reflector and then a dichroic beam splitter and then therefrom impinge onto a forth selected element; and
at least one reflector and then impinge onto a forth selected element.

16. A system as in claim 15 which the forth selected element, upon receiving said reflected beam of electromagnetic radiation produces a spectrum of dispersed wavelengths which are directed toward a forth detector.

17. A system as in claim 16, in which at least one selection from the group consisting of:
said forth selected element is designed to optimally structure the range of wavelengths exiting therefrom;
said forth detector is designed to optimally detect the range of wavelengths input thereinto by said first and second selected elements respectively;
is enabled.

18. A system as in claim 1, which specifically involves a beam of spectroscopic electromagnetic radiation from said sample that is caused to impinge onto a grating or a combination dichroic beam splitter-prism which produces said spectrum of diffracted dispersed wavelengths, which spectrum is directed to enter a detector; and simultaneously produces said altered spectral content reflected beam of electromagnetic radiation which is directed to interact with a dichroic beam splitter that causes said altered spectral content reflected beam of electromagnetic radiation to split into two beams, both of which are directed to separate selections from the group consisting of:
a grating which when presented with an incident spectroscopic beam of electromagnetic radiation produces a spectrum of diffracted dispersed wavelengths and simultaneous therewith an altered spectral content reflected beam of electromagnetic radiation;
a combination dichroic beam splitter-prism which when presented with a spectroscopic beam of electromagnetic radiation produces a spectrum of wavelengths that transmit through and exit from said prism, and simultaneous therewith an altered spectral content reflected beam of electromagnetic radiation;
such that the spectrum of dispersed wavelengths that exit from a present grating or combination dichroic beam splitter-prism are each caused to enter separate detectors.

19. A system as in claim 1 wherein the spectroscopic beam of electromagnetic radiation from said sample which is caused to impinge onto a first selected element such that a spectrum of dispersed wavelengths is produced and directed toward a first detector, simultaneous with production of an altered spectral content reflected beam of electromagnetic radiation which is directed to impinge on a second selected element which likewise produces a spectrum of dispersed wavelengths which are directed toward a second detector, is the output beam of an ellipsometer or polarimeter which exits the analyzer thereof.

20. A system as in claim 1, which specifically involves a beam of spectroscopic electromagnetic radiation from said sample that is caused to interact with a sequence of elements comprising:
a first grating and first and first detector, wherein the reflected beam exiting said first grating is a zero order beam and is directed to a second grating and second detector.

21. A system as in claim 1, which specifically involves a beam of spectroscopic electromagnetic radiation from said sample that is caused to interact with a sequence of elements comprising:
a first grating and first detector, wherein the reflected beam exiting said first grating is a zero order beam and is directed to a first combination dichroic beam splitter-prism and second detector.

22. A system as in claim 1, which specifically involves a beam of spectroscopic electromagnetic radiation from said sample that is caused to interact with a sequence of elements comprising:
a dichroic beam splitter which sends first and second ranges of dispersed wavelengths, which are substantially above and below a certain wavelength, respectively, each to a selection from the group consisting of:
a first grating and first detector, wherein the reflected beam exiting said first grating is a zero order beam and is directed to a second grating and second detector; and
a first grating and first detector, wherein the reflected beam exiting said first grating is a zero order beam and is directed to a first dichroic beam splitter-prism combination and second detector.

23. A system as in claim 1, which specifically involves a beam of spectroscopic electromagnetic radiation from said sample that is caused to interact with a sequence of elements comprising:
a first combination dichroic beam splitter-prism and first detector, and wherein the reflected beam reflecting from said first combination dichroic beam splitter-prism is directed to a first grating and second detector.

24. A system as in claim 1, which specifically involves a beam of spectroscopic electromagnetic radiation from said sample that is caused to interact with a sequence of elements comprising:
a first grating and first detector, wherein the reflected beam produced by said first grating is a zero order beam and is directed to a second grating and second detector, and in which the reflected beam produced by said second grating is a zero order beam directed to a third grating and third detector.

25. A system as in claim 1, which specifically involves a beam of spectroscopic electromagnetic radiation from said sample that is caused to interact with a sequence of elements comprising:
a first grating and first detector, wherein the reflected beam produced by said first grating is a zero order beam and is directed to a first combination dichroic beam splitter-prism and second detector, and in which the reflected beam reflected from said first combination dichroic beam splitter-prism is directed to a third grating and third detector via a dichroic beam splitter.

26. A system as in claim 1, which specifically involves a beam of spectroscopic electromagnetic radiation from said sample that is caused to interact with a sequence of elements comprising:
a first grating and first detector, wherein the reflected beam produced by said first grating is a zero order beam and is directed to a second grating and second detector, and in which the reflected beam produced by said second grating is a zero order beam and is directed to a first dichroic beam splitter-prism combination and third detector.

27. A system as in claim 1, which specifically involves a beam of spectroscopic electromagnetic radiation from said sample that is caused to interact with a sequence of elements comprising:
a first grating and first detector, wherein the reflected beam produced by said first grating is a zero order beam and is directed to a first combination dichroic beam splitter-prism and second detector, and in which the reflected beam reflected from said first combination dichroic beam splitter-prism is directed to a second dichroic beam splitter-prism combination and third detector via a beam splitter.

28. A system as in claim 1, which specifically involves a beam of spectroscopic electromagnetic radiation from said sample that is caused to interact with a sequence of elements comprising:
a first combination dichroic beam splitter-prism and first detector, wherein the reflected beam reflected by said first combination dichroic beam splitter-prism is directed to a second grating and second detector, and in which the reflected beam produced by said second grating is a zero order beam and is directed to a third grating and third detector.

29. A system as in claim 1, which specifically involves a beam of spectroscopic electromagnetic radiation from said sample that is caused to interact with a sequence of elements comprising:
a first combination dichroic beam splitter-prism and first detector, wherein the reflected beam reflected from said first combination dichroic beam splitter-prism is directed to a second dichroic beam splitter-prism combination and second detector, and in which the reflected beam reflected from said second combination dichroic beam splitter-prism is directed to a third grating and third detector via a dichroic beam splitter.

30. A system as in claim 1, which specifically involves a beam of spectroscopic electromagnetic radiation from said sample that is caused to interact with a sequence of elements comprising:
a first combination dichroic beam splitter-prism and first detector, wherein the reflected beam reflected from said first combination dichroic beam splitter-prism is directed to a first grating and second detector, and in which the reflected beam produced by said second grating is a zero order beam and is directed to a second combination dichroic beam splitter-prism and third detector.

31. A system as in claim 1, which specifically involves a beam of spectroscopic electromagnetic radiation from said sample that is caused to interact with a sequence of elements comprising:
a first combination dichroic beam splitter-prism and first detector, wherein the reflected beam reflected from said first combination dichroic beam splitter-prism is directed to a second combination dichroic beam splitter-prism and second detector, and in which the reflected beam reflected from said combination second dichroic beam splitter-prism is directed to a third combination dichroic beam splitter-prism and third detector via a beam splitter.

32. A system as in claim 1, wherein the spectrum of dispersed diffracted wavelengths produced by said grating is a + or − order spectrum.

33. A system as in claim 1, in which range is limited to between greater than 1000, to about 2500 nm.

34. A system for practicing a method of investigating a sample, said the method being:
a) providing a sample investigation system selected from the group consisting of:
  a reflectometer;
  a spectrophotometer;
  an ellipsometer; and
  a polarimeter;
comprising:
  a) a source of a beam of a spectroscopic beam of electromagnetic radiation;
  b) a stage for supporting a sample; and
  c) a detector system for monitoring electromagnetic radiation;
said system being distinguished in that said source of a high intensity, highly directional spectroscopic beam of electromagnetic radiation is a super continuum laser that provides a coherent spectrum of electromagnetic radiation wavelengths within a range of about 400 to about 2500 nm, that results from interaction of a pulsed laser and multiple non-linear processes to cause extensive spectral broadening;
said system further comprising a speckle reducer in the form of a selection from the group consisting of:
  a beam diffuser;
  a fly's-eye beam homogenizer;
  a rotating beam diffuser;
  a piezoelectric electric crystal driven beam diffuser;
  an electronic means to shorten temporal coherence length;
said speckle reducer serving to reduce wild swings in intensity of electromagnetic radiation as a function of position in a beam resulting from interference effects between different coherent wavelengths in said extensively broadened spectrum;
wherein said detector system comprises means for producing a plurality of separate wavelength ranges from a spectroscopic beam incident thereupon, said system comprising a sequence of at least two elements, each thereof being selected from the group consisting of:
  a grating which when presented with an incident spectroscopic beam of electromagnetic radiation produces a spectrum of diffracted dispersed wavelengths and simultaneous therewith an altered spectral content reflected beam of electromagnetic radiation;
  a combination dichroic beam splitter-prism which when presented with a spectroscopic beam of electromagnetic radiation produces a spectrum of dispersed wavelengths that transmit through and exit from said prism, and simultaneous therewith an altered spectral content reflected beam of electromagnetic radiation;
such that in use a spectroscopic beam of electromagnetic radiation provided by said supercontinuum laser and speckle reducer is caused to interact with a sample placed upon said stage, and then impinge onto a first selected element such that a spectrum of dispersed wavelengths is produced and directed toward a first detector, simultaneous with production of a reflected altered spectral content reflected beam of electromagnetic radiation which is directed to impinge on a second selected element which likewise produces a spectrum of dispersed wavelengths which are directed toward a second detector;
  b) causing a spectroscopic beam of speckle reduced electromagnetic radiation provided by said super continuum laser and speckle reducer to interact with a sample on said stage, then impinge onto a first selected element such that a spectrum of dispersed wavelengths is produced and directed toward a first detector, simultaneous with production of a reflected altered spectral content reflected beam of electromagnetic radiation which is directed to impinge on a second selected element which likewise produces a spectrum of dispersed wavelengths which are directed toward a second detector.

35. A system as in claim 34 further comprises providing a beam splitter between said first and second selected elements which each produce a spectrum of dispersed wavelengths which are directed toward a second detector; and
causing the reflected altered spectral content reflected beam of electromagnetic radiation which is directed to impinge on a beam splitter so that it directs at least some of said beam into onto a third selected element which produces a spectrum of dispersed wavelengths and directs it into a third detector, while also directing at least some of said beam toward said second selected element which continues to direct the spectrum of dispersed wavelengths produced thereby toward said second detector.

36. A system for practicing a method of investigating a sample, said the method being:
a) providing a sample investigation system selected from the group consisting of:
  a reflectometer;
  a spectrophotometer;
  an ellipsometer; and
  a polarimeter;
comprising:
  a) a source of a beam of a spectroscopic beam of electromagnetic radiation;
  b) a stage for supporting a sample; and
  c) a detector system for monitoring electromagnetic radiation;
said system being configured such that a beam of electromagnetic radiation produced by said source is directed to interact with a sample placed on said stage for supporting a sample so that it interacts with said sample and then proceeds, as the beam of electromagnetic radiation, into said detector;
said detector system further comprising means for producing a plurality of separate wavelength ranges from a spectroscopic beam incident thereupon, said system comprising a sequence of at least two elements, each thereof being selected from the group consisting of:
  a grating which when presented with an incident spectroscopic beam of electromagnetic radiation produces a spectrum of diffracted dispersed wavelengths and simultaneous therewith an altered spectral content reflected beam of electromagnetic radiation; and
  a combination dichroic beam splitter-prism which when presented with a spectroscopic beam of electromagnetic radiation produces a spectrum of dispersed wavelengths that transmit through and exit from said prism, and simultaneous therewith an altered spectral content reflected beam of electromagnetic radiation;
such that in use a spectroscopic beam of electromagnetic radiation from said source thereof is caused to interact with a sample placed on said stage, and then impinge onto a first selected element such that a spectrum of dispersed wavelengths is produced and directed toward a first detector, simultaneous with production of a reflected altered spectral content reflected beam of electromagnetic radiation which is directed to impinge on a second selected element which likewise produces a spectrum of dispersed wavelengths which are directed toward a second detector;

said system being distinguished in that said source of a high intensity, highly directional spectroscopic beam of electromagnetic radiation is a super continuum laser that provides a coherent spectrum of electromagnetic radiation wavelengths within a range of about 400 to about 2500 nm, that results from interaction of a pulsed laser and multiple non-linear processes to cause extensive spectral broadening; said system further comprising a speckle reducer, said speckle reducer serving to reduce wild swings in intensity of electromagnetic radiation as a function of position in a beam resulting from interference effects between different coherent wavelengths in said extensively broadened spectrum;

b) causing a spectroscopic beam of speckle reduced electromagnetic radiation provided by said super continuum laser and speckle reducer to interact with a sample on said stage, then enter said detector system.

* * * * *